(12) United States Patent
Kagermeier

(10) Patent No.: US 7,787,929 B2
(45) Date of Patent: Aug. 31, 2010

(54) CONTROL SYSTEM FOR MEDICAL EQUIPMENT

(75) Inventor: Robert Kagermeier, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1590 days.

(21) Appl. No.: 10/895,722

(22) Filed: Jul. 21, 2004

(65) Prior Publication Data

US 2005/0025706 A1 Feb. 3, 2005

(30) Foreign Application Priority Data

Jul. 25, 2003 (DE) ................. 103 34 073

(51) Int. Cl.
*A61B 5/05* (2006.01)
(52) U.S. Cl. .................. 600/407; 378/20; 382/128
(58) Field of Classification Search ............... 345/156; 378/8, 20; 710/1; 600/407
See application file for complete search history.

(56) References Cited

U.S. PATENT DOCUMENTS

| | | | |
|---|---|---|---|
| 6,175,610 B1 * | 1/2001 | Peter | ............... 378/8 |
| 7,400,744 B2 * | 7/2008 | Nichani et al. | ............... 382/103 |
| 2002/0104163 A1 | 8/2002 | Reimann | |
| 2004/0046736 A1 * | 3/2004 | Pryor et al. | ................. 345/156 |
| 2004/0103222 A1 * | 5/2004 | Carr et al. | ...................... 710/1 |
| 2006/0187192 A1 | 8/2006 | Kagermeier et al. | |

FOREIGN PATENT DOCUMENTS

DE 44 39 298 A1 6/1996

* cited by examiner

Primary Examiner—Long V Le
Assistant Examiner—Nicholas L Evoy
(74) Attorney, Agent, or Firm—Brinks, Hofer, Gilson & Lione

(57) ABSTRACT

A control system for medical equipment comprises an examination/treatment system, an optical detection system which is operably affixed to the examination/treatment system and configured to collect data corresponding to detected gestural inputs made by an operator in relation to a targeted examination/treatment area on a patient positioned on a patient examination apparatus, and an evaluation system configured to adjust operation parameters of the examination/treatment system as a function of the collected gestural input data communicated by the optical detection system.

17 Claims, 1 Drawing Sheet

CONTROL SYSTEM FOR MEDICAL EQUIPMENT

BACKGROUND

The invention relates, in general, to medical equipment, and in particular to a control system of a medical imaging system, such as an x-ray system or magnetic resonance (MRI) system. The invention also relates to a method for operating a medical examination and treatment system.

From German Patent Disclosure DE 101 03 331 A1, an imaging medical examination system, in particular for computer tomography (CT) or magnet resonance imaging (MRI), is known which is intended for three-dimensional scanning of a patient. The patient is introduced into an opening of a housing, which, for example, encloses a magnet, and is passed through the housing opening incrementally or continuously until an area of the patient to be examined has been scanned completely. The area to be examined and a type of examination are typically selected, in a so-called topographic or top-view image, using inputs by a mouse and keyboard on a control console at a distance from the patient. In x-ray equipment, one may, for example, project a light-beam localizer of a multileaf diaphragm onto the patient so as to position the patient in such a way that the area to be examined is within an imaging range of the x-ray system. In such case, a precise adjustment of the examination/treatment area or the positioning of the patient typically entails considerable effort.

SUMMARY

The present invention is defined by the appended claims. This description summarizes some aspects of the present embodiments and should not be used to limit the claims.

Both a control system for medical equipment and a method are disclosed which enable a substantially simple and reliable determination of an examination and/or treatment area in an examination or treatment using medical equipment, in particular using a system that uses an imaging process.

The control system includes an examination/treatment system for medical equipment, an optical detection system, and an evaluation system that cooperates with the optical detection system and the medical equipment. The medical equipment is for instance an imaging examination system, such as an x-ray system, in particular a CT system or an MRI system. Medical equipment, in this context, may also be understood to be a therapy system, such an irradiation system.

The optical detection system is provided to detect gestural inputs, i.e. physical gesture inputs such as hand motions, of a machine operator or user and may not necessarily use visible light exclusively. The data detected via gestural inputs are communicated to the evaluation system, which as a function of these data may adjust parameters pertaining to the operation of the medical equipment.

Using the operation parameters, a volumetric area to be examined or treated, for example a scanning area in the case of an examination system, is substantially defined. If the patient is on a patient examination table, such as a narrow cot or a board for a gurney, then the area of the patient to be examined or treated may be unambiguously defined in a local relationship with the examination table via the specification of the volumetric area. In a substantially user-friendly way, the examination/treatment area for which the machine operator may specify appropriate volumetric boundaries close to the patient via gestures that can be classified as intuitive, can be selected.

In one embodiment, in addition to the gestures of the machine operator, the positioning of the patient on the examination table is detected by the optical detection system. The user, such as the physician, may be provided with a capability of not, or not only, making the gestural inputs in geometric relationship with the medical equipment but also in direct relationship to the patient, for instance by pointing to areas on the body of the patient that are to be examined.

The control system for medical equipment preferably has a display device, which is disposed such that it is within a field of view of the user performing the gestural inputs. Alternatively or in addition, however, a display device remote from the patient may be provided as well. In relatively close local relationship with the display device, for instance in the form of a touch-sensitive screen, one may preferably be able to input treatment parameters and/or to correct the parameters selected via the gestural inputs.

In another embodiment, the optical detection system may have a transit-time measurement system, which makes it relatively simple and fast to generate three-dimensional data. A 3D (three dimensional) camera using the transit-time process is known in principle, for instance from German Patent Disclosure DE 44 39 298 A1. In one feature, the detection system may have both a 3D camera and at least one camera intended for recording 2D (two-dimensional) data. Via a data linkage of the 3D camera with the 2D camera or cameras, relatively fast and reliable detection and evaluation of motions in three-dimensional space may be possible at relatively little expense for equipment and computation. Alternatively, the optical detection system employs 2D cameras exclusively. In that case, triangulation measurements make stereo image evaluation possible; i.e. three-dimensional data may be ascertained from two-dimensional image data. In comparison to the transit-time measurement system, the triangulation measurements may have a comparatively higher computation effort and a comparatively lower effort in the field of the optical recording systems.

In another embodiment, and in addition to the optical detection system, the control system has a speech recognition system cooperating with the optical detection system and having at least one recording device. The at least one recording device may be preferably provided for a cordless signal transmission, for instance by radio or infrared, to the evaluation system. In addition, a microphone to be worn by the user is equally suitable as a number of microphones installed in fixed places in relation to the examination/treatment system. In the case of a plurality of fixedly installed microphones, the optical detection system may cooperate with the recording device to determine via the image evaluation which of the plurality of fixedly installed microphones should be activated to achieve the best possible recording quality.

Independently of how the speech recognition system may be designed, the speech recognition system may cooperate in real time with the optical detection system. For instance, an input to the optical detection system made via a gesture on the part of the user is confirmed or made concrete via a speech input. As a result, a substantially high reliability of the combined gesture and speech input may be attained.

Furthermore, the user may have the capability, after the inputting, of monitoring the selected parameters in displayed form on the display device and optionally changing them. Both the gestural input and the speech input, depending on the type of medical equipment, are provided not only for defining the examination and/or treatment area but also for selecting the examination method and/or further parameters.

The control system for medical equipment is preferably linked with a medical information system, which may provide access to electronic patient files. The linkage with the relative data of the information system can preferably be achieved in a substantially user-friendly, time-saving way with the aid of the speech recognition system that cooperates with the optical detection system. Moreover, the data coupling of the evaluation system with the medical information system offers a relatively simple capability of examining the parameters, selected by the user via gestural inputs and/or speech inputs, for the examination and/or treatment, for plausibility, correctness and/or accuracy. If the parameters selected by the user are not in agreement with the data stored in memory in the medical information system, then a warning can optionally be issued via the display device.

One advantageous feature of one embodiment may be that an optical detection system with real-time image processing enables the machine operator of the medical equipment to input the examination and/or treatment region intuitively and near the patient; operator-control inputs via keyboards or pointer devices such as a mouse are thus reduced to a minimum or may be dispensed with entirely.

Illustrative and exemplary embodiments of the invention are described in further detail below with reference to and in conjunction with the figures.

DETAILED DESCRIPTION

Figure 1:
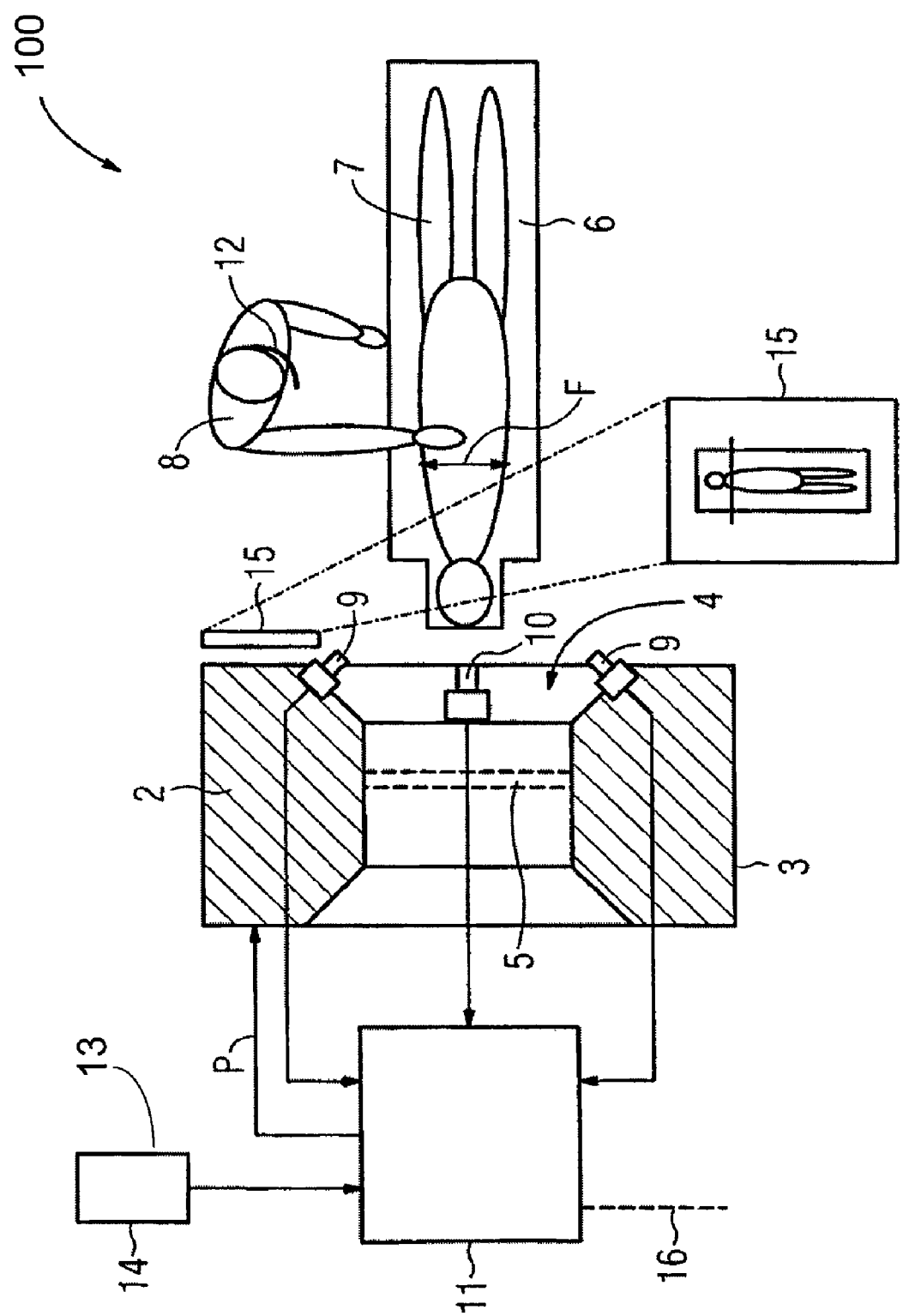
FIG. 1 is a schematic illustrating an embodiment of a medical control system of a CT system, as an example of medical equipment.

While the present invention may be embodied in various forms, there is shown in the drawings and will hereinafter be described some exemplary and non-limiting embodiments, with the understanding that the present disclosure is to be considered an exemplification of the invention and is not intended to limit the invention to the specific embodiments illustrated.

In this application, the use of the disjunctive is intended to include the conjunctive. The use of definite or indefinite articles is not intended to indicate cardinality. In particular, a reference to "the" object or "a" object is intended to denote also one of a possible plurality of such objects.

FIG. 1 shows an embodiment of a medical control system 100 that includes a CT system 2, as an example of medical equipment, which will here generally be referred to as an examination/treatment system.

In a schematic depiction, the CT system 2 has a housing or gantry 3 with an opening 4 in which the scanning region 5 is disposed. A patient 7 lying on an examination table 6 is pushed through the scanning region 5 and examined in individual cross-sectional planes. A cross-sectional area through the upper body of the patient 7, which area is to be examined, is represented by a double arrow and marked F.

Before beginning the examination of the patient, an operator 8 situated near the examination/treatment system 2 must define the examination region, which in general includes a plurality of parallel examination regions, such as the cross-sectional area F shown as an example. For that purpose, an optical detection system is provided, which in this exemplary embodiment includes two 2D cameras 9 and one 3D camera 10. The 2D cameras 9 are equivalent to conventional video cameras suitable for producing two-dimensional images. As for the 3D camera 10, a so-called time-of-flight camera that employs the transit-time method and uses a semiconductor-based 3D image sensor is employed. This 3D camera 10, without relatively major computation effort, generates 3D data in real time that are additionally available for evaluation for the sake of two-dimensional image information. All the cameras 9, 10 are operably linked with an evaluation system 11.

The operator 8, with a relatively simple hand motion, inputs a boundary of the region to be examined of the patient 7 into the evaluation system 11 via the cameras 9, 10. In addition, speech input is provided, via a headset in the form of a recording device 12 and a radio receiver 13 which communicates with the recording device and is connected to the evaluation system 11. A speech recognition system thus provided can, as an alternative to the recording device 12 that can be worn by the user 8, have fixedly installed microphones as well. Along with the gestural inputs, the user 8 provides speech inputs, such as "scanning region begins here" or "scanning region ends here", that confirm or concretize gestural input information.

The speech input is compared in the evaluation system 11 with the gestural input and monitored for plausibility and correctness. As such, relatively high recognition certainty is achieved. Regardless of the type of microphone 12 or microphones 12 employed, the control system 100 is usable and can be operated intuitively, including the speech recognition system 14, after minimal training.

With the aid of the data detected via speech and gestural inputs, the evaluation system 11 defines operation parameters P, which are used to trigger the examination equipment 2. The adjustment of the operation parameters P is displayed to the user 8 via a display device 15, which is additionally shown enlarged in the drawing in a symbolically projected view. The display device 15 has a touch-sensitive screen, which may make it relatively simple to correct the data detected by the speech and gestural inputs. Data input with any other arbitrary data acquisition device, in particular a keyboard or a mouse, is also possible. It is equally possible to correct the operation parameters by new speech and gestural inputs, and each correction is visible in real time on the display device 15.

The evaluation system 11 is operably linked with a medical information system (not shown). The link is symbolically indicated as a data line 16. Relatively easy access to the patient-relevant data stored in memory in the information system can be retrieved via the speech recognition system 14. Furthermore, a calibration is provided between the data acquired via speech and gestural inputs and the information made available by the medical information system, in particular an electronic patient file This calibration may enable, if the data are not consistent, the issuance of reports accordingly using the display device 15.

The invention claimed is:

1. A control system for medical equipment, comprising:
   an examination or treatment system;
   an optical detection system operable to detect gestural inputs made to designate a location in an examination or treatment area by an operator;
   an evaluation system operable to adjust operation parameters of the examination or treatment system as a function of the gestural inputs, and
   a speech recognition system which cooperates with the evaluation system, the speech recognition system having a recording device,
   wherein an adjustment of recording parameters of the speech recognition system is a function of the data recorded via the optical detection system.

2. The control system of claim 1, wherein the operation parameters define a spatial relationship of the examination or treatment area to the patient.

3. The control system of claim 2, wherein the optical detection system is operable to detect a positioning of the patient on an examination table.

4. The control system of claim 1, further comprising a display device, the display device operable to display the adjustment of operation parameters.

5. The control system of claim 1, wherein the optical detection system comprises a transit-time measurement system.

6. The control system of claim 1, wherein the optical detection system comprises a plurality of cameras.

7. The control system of claim 6, wherein the plurality of cameras provides a stereo image evaluation of the patient to be examined.

8. The control system of claim 6, wherein the plurality of cameras correspond to a stereo image evaluation of the examination or treatment area of the patient to be examined.

9. The control system of claim 1, wherein the recording device is in wireless communication with the evaluation system.

10. The control system of claim 1, further comprising a plurality of recording devices operable to be triggered as a function of the data recorded via the optical detection system.

11. The control system of claim 1, further comprising a medical information system in communication with the evaluation system.

12. The control system of claim 4, further comprising a speech recognition system which cooperates with the evaluation system, the speech recognition system having a recording device.

13. A method for operating a medical examination or treatment system, the method comprises:
    detecting a gestural input made to designate a location in an examination or treatment area with an optical detection system;
    communicating data corresponding to the detected gestural input to an evaluation system;
    determining operation parameters of the examination or treatment system as a function of the gestural input data; and
    correlating gestural input data detected by the optical detection system with speech data detected by a speech recognition system.

14. The method of claim 13 further comprising confirming gestural input data detected by the optical detection system with speech data detected by the speech recognition system.

15. The method of claim 13 further comprising:
    activating a gestural input in response to the speech data.

16. The control system of claim 1, wherein the gestural inputs are made by pointing to areas on a body of the patient.

17. The method of claim 13, wherein the gestural input is made by pointing to areas on a body of the patient.

* * * * *